United States Patent
Cote et al.

(10) Patent No.: US 9,579,094 B2
(45) Date of Patent: *Feb. 28, 2017

(54) IRIS EXPANDER

(71) Applicant: BEAVER-VISITEC INTERNATIONAL (US), INC., Lake Forest, IL (US)

(72) Inventors: Dana M. Cote, Boxford, MA (US); James J. Hughes, Dracut, MA (US)

(73) Assignee: Beaver-Visitec International (US), Inc., Waltham, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 14/553,642

(22) Filed: Nov. 25, 2014

(65) Prior Publication Data

US 2015/0080665 A1    Mar. 19, 2015

Related U.S. Application Data

(63) Continuation of application No. 14/216,013, filed on Mar. 17, 2014, now Pat. No. 8,900,136.

(Continued)

(51) Int. Cl.
*A61B 1/32* (2006.01)
*A61B 17/02* (2006.01)

(Continued)

(52) U.S. Cl.
CPC ...... *A61B 17/0231* (2013.01); *A61B 17/0293* (2013.01); *A61F 9/00736* (2013.01);

(Continued)

(58) Field of Classification Search
CPC ............. A61B 17/0231; A61B 17/0293; A61F 9/00736
See application file for complete search history.

(56) References Cited

U.S. PATENT DOCUMENTS 2,053,868 A    9/1936  Grosso
2,845,925 A    8/1958  Jayle (Continued)

FOREIGN PATENT DOCUMENTS

AU    712377        11/1998
CN    200966677 Y   10/2007

(Continued)

OTHER PUBLICATIONS

Rumpler, Clamping ring for temporary implantation in the human eye dilating the pupil, Oct. 2007, DE202007010335 U1 translated by google from German.*

(Continued)

*Primary Examiner* — Ellen C Hammond
(74) *Attorney, Agent, or Firm* — BudzynFortunato IP Law, LLC

(57) ABSTRACT

In a first aspect of the subject invention, an iris expander is provided which includes a non-metallic, unitary, multi-segmented body which is expandable from a first state to a second state. The second state defines a larger footprint than the first state with the body being defined by a plurality of segments connected by living hinges. In a further aspect, an iris expander is provided which includes a multi-segmented body that is expandable from a first state to a larger-footprint second state. At least one aperture is formed in the body with a channel extending therefrom embedded in the body such that no portion thereof is exposed externally of the body. The channel is formed to accommodate a portion of an instrument for causing adjustment of the body with avoidance of direct contact of the instrument with the tissue of the iris.

11 Claims, 18 Drawing Sheets

Related U.S. Application Data

(60) Provisional application No. 61/788,350, filed on Mar. 15, 2013.

(51) Int. Cl.
*A61F 9/007* (2006.01)
*A61B 17/00* (2006.01)

(52) U.S. Cl.
CPC .............. *A61B 2017/00862* (2013.01); *A61B 2017/00955* (2013.01)

(56) References Cited

U.S. PATENT DOCUMENTS

| | | | |
|---|---|---|---|
| 3,490,455 A | 1/1970 | Illig | |
| 4,037,589 A | 7/1977 | McReynolds | |
| 4,257,406 A | 3/1981 | Schenk | |
| 4,387,706 A * | 6/1983 | Glass | A61B 17/0231 600/208 |
| 4,782,820 A | 11/1988 | Woods | |
| 4,991,567 A | 2/1991 | McCuen, II et al. | |
| 5,163,419 A * | 11/1992 | Goldman | A61B 17/0231 600/206 |
| 5,174,279 A | 12/1992 | Cobo et al. | |
| 5,267,553 A | 12/1993 | Graether | |
| 5,299,564 A | 4/1994 | Sabatino | |
| 5,318,011 A | 6/1994 | Federman et al. | |
| 5,322,054 A * | 6/1994 | Graether | A61B 17/0231 269/303 |
| 5,374,272 A | 12/1994 | Arpa et al. | |
| 5,427,088 A | 6/1995 | Graether | |
| 5,441,045 A | 8/1995 | Federman et al. | |
| 5,514,076 A | 5/1996 | Ley | |
| 5,607,446 A | 3/1997 | Beehler et al. | |
| 5,634,884 A | 6/1997 | Graether | |
| 5,716,328 A | 2/1998 | Grieshaber et al. | |
| 5,807,244 A | 9/1998 | Barot | |
| 5,846,192 A * | 12/1998 | Teixido | A61B 17/02 600/201 |
| 6,068,643 A * | 5/2000 | Milverton | A61F 9/007 606/107 |
| 6,332,866 B1 | 12/2001 | Grieshaber et al. | |
| 6,561,974 B1 | 5/2003 | Grieshaber et al. | |
| 6,620,098 B1 | 9/2003 | Milverton | |
| D573,711 S | 7/2008 | Johnson et al. | |
| 8,323,296 B2 | 12/2012 | Malyugin | |
| 8,439,833 B2 | 5/2013 | Christensen et al. | |
| D686,729 S | 7/2013 | Christensen et al. | |
| 8,496,583 B1 | 7/2013 | Reynard | |
| 2003/0092970 A1 | 5/2003 | Lee | |
| 2007/0191941 A1 | 8/2007 | Dick et al. | |
| 2008/0188860 A1 | 8/2008 | Vold | |
| 2008/0243139 A1 | 10/2008 | Dusek | |
| 2012/0289786 A1 | 11/2012 | Dusek | |
| 2013/0131458 A1 | 5/2013 | Malyugin | |
| 2013/0267988 A1 | 10/2013 | Sussman et al. | |
| 2014/0221759 A1 | 8/2014 | Mackool et al. | |

FOREIGN PATENT DOCUMENTS

| | | |
|---|---|---|
| DE | 202007010335 U1 | 11/2007 |
| EP | 0769271 A1 | 4/1997 |
| FR | 2827497 A1 | 1/2003 |
| RU | 2295941 C1 | 3/2007 |
| RU | 122576 U1 | 10/2012 |
| WO | 9314703 | 8/1993 |
| WO | 2004010876 A1 | 2/2004 |
| WO | 2011143018 A2 | 11/2011 |
| WO | 2012037550 A1 | 3/2012 |

OTHER PUBLICATIONS

Print-out from http://www.fci-ophthalmics.com/cataract#morcher_pupil; FCI Ophthalmics; Jul. 21, 2014, pp. 5-6, U.S.

Xpand Iris Speculum, print-out from website: http://www.diamatrix.com/xpandintro.html, 2014.

Search Report and Written Opinion from WIPO PCT Application No. PCT/US2014/030550, dated Aug. 27, 2014.

* cited by examiner

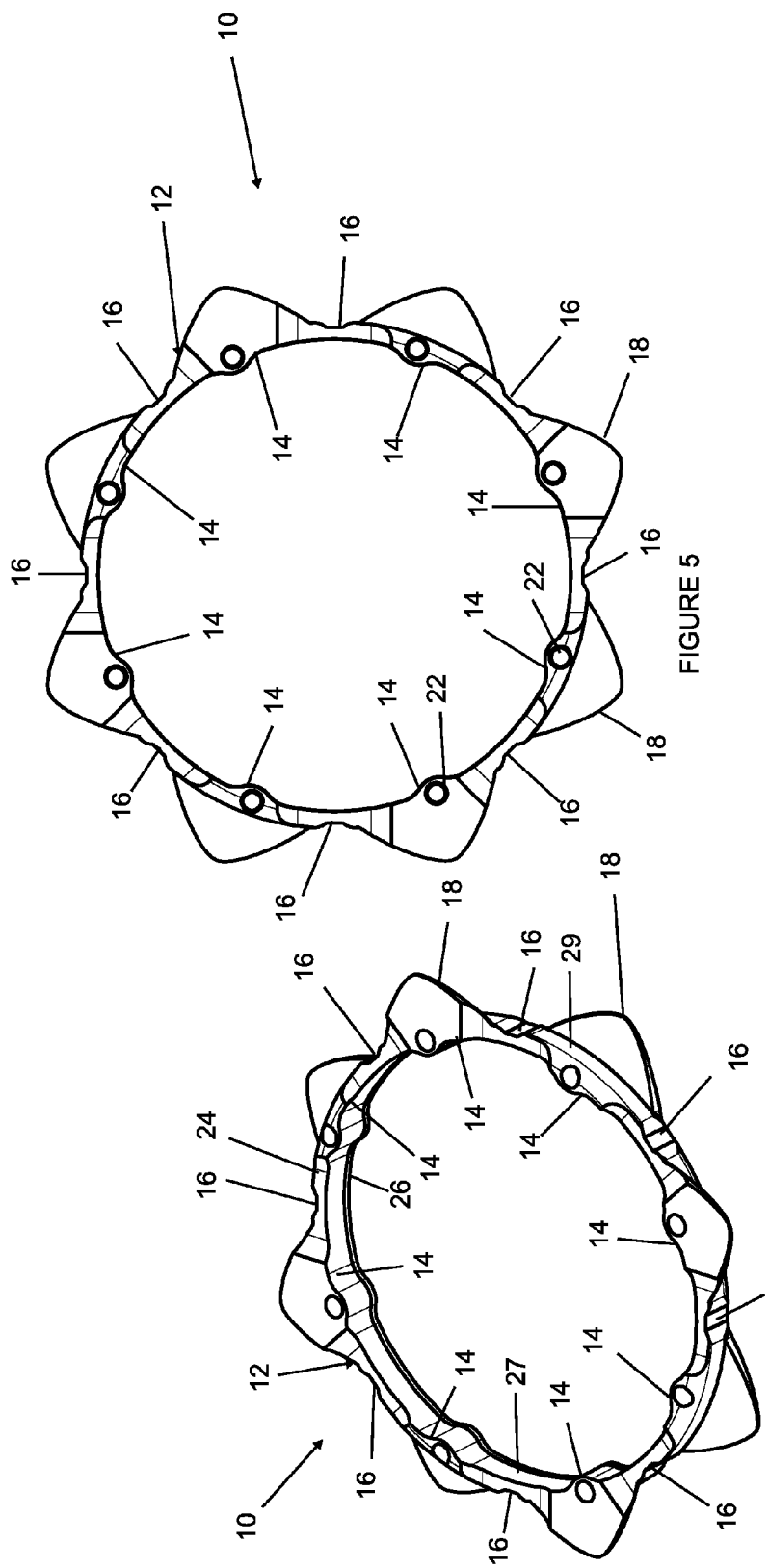
FIGURE 5
FIGURE 4
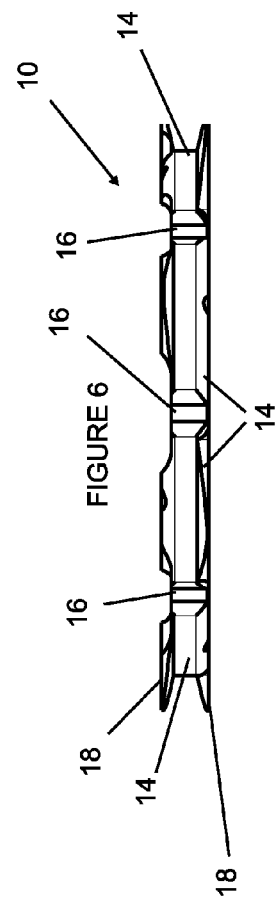
FIGURE 6

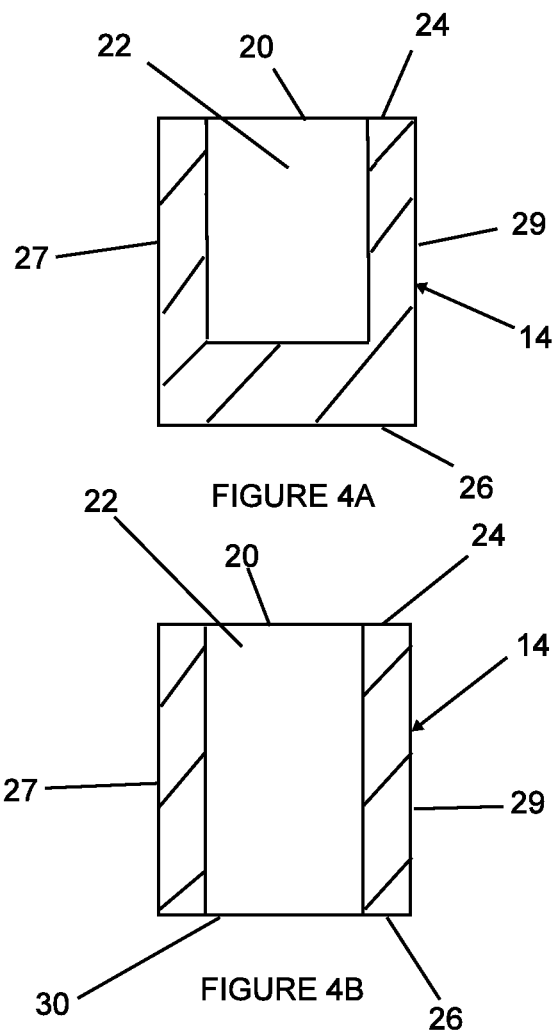

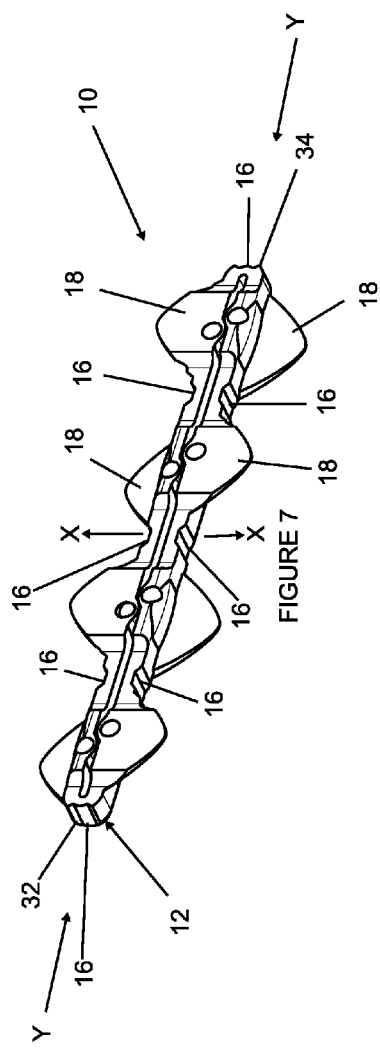
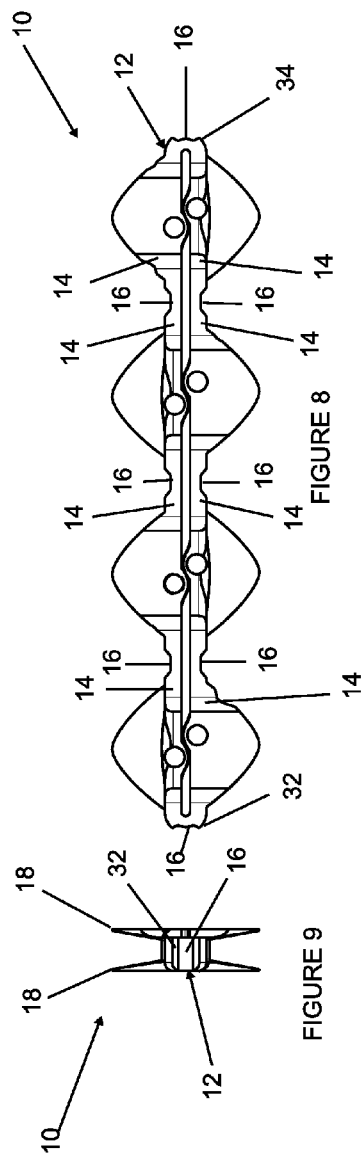
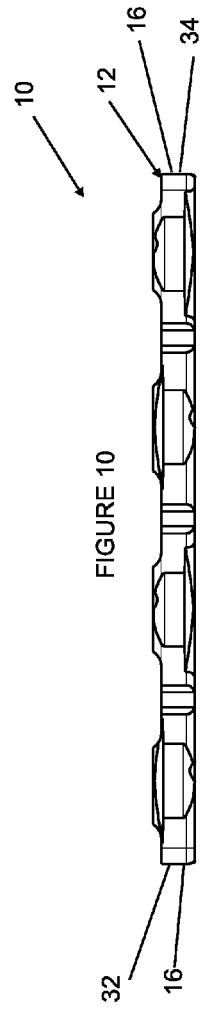

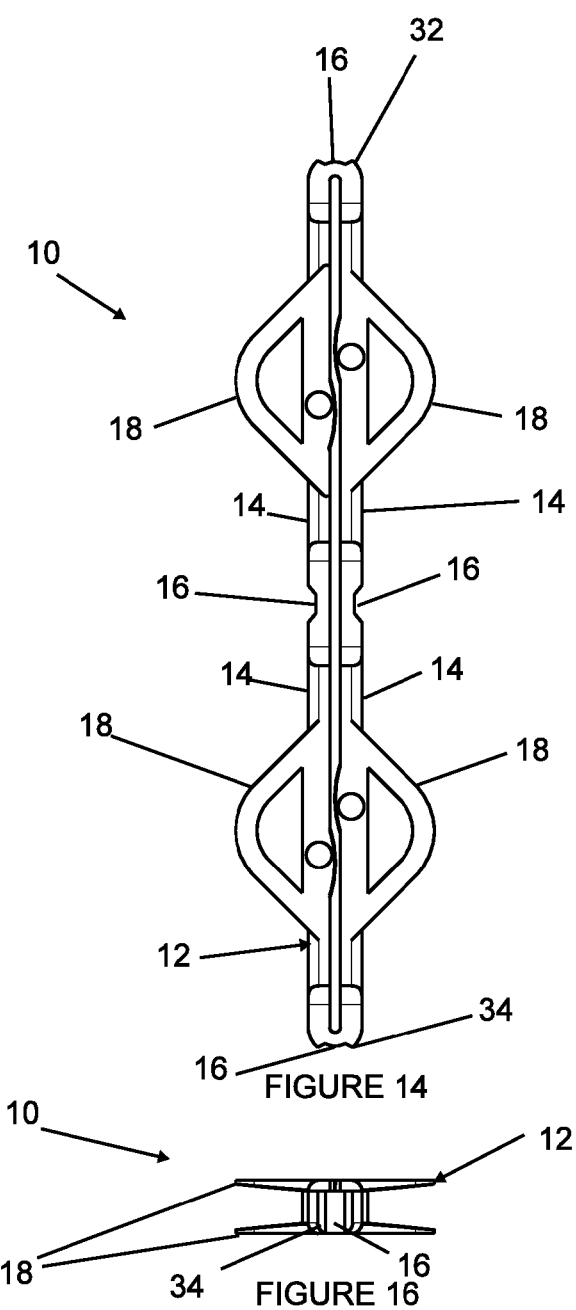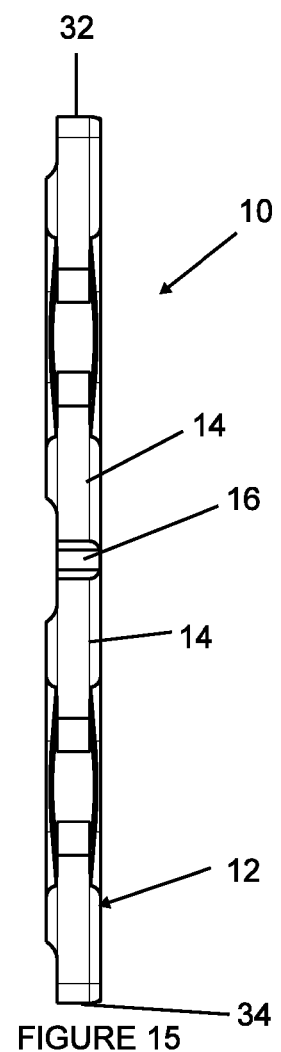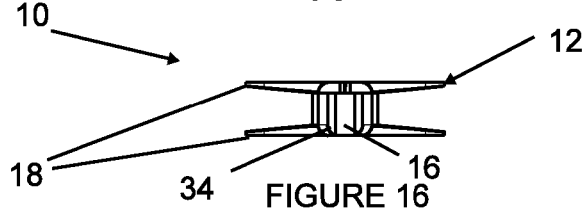
FIGURE 14
FIGURE 15
FIGURE 16

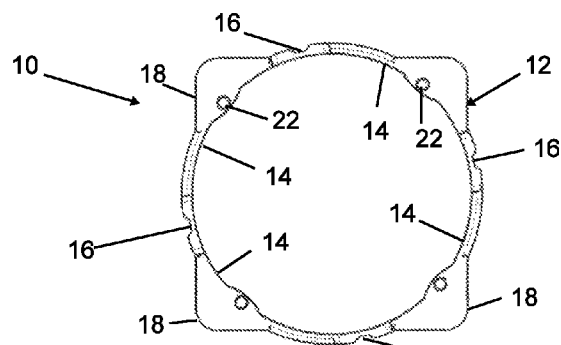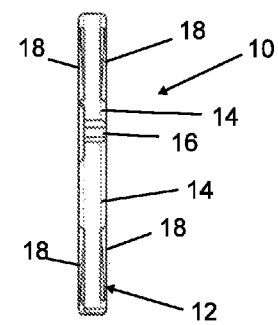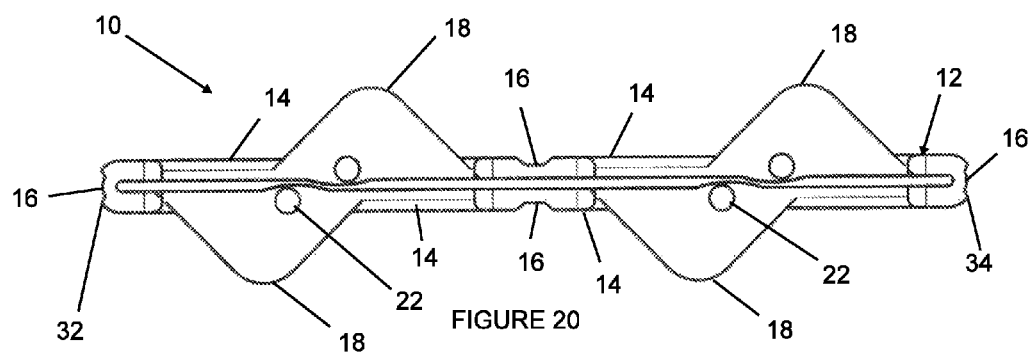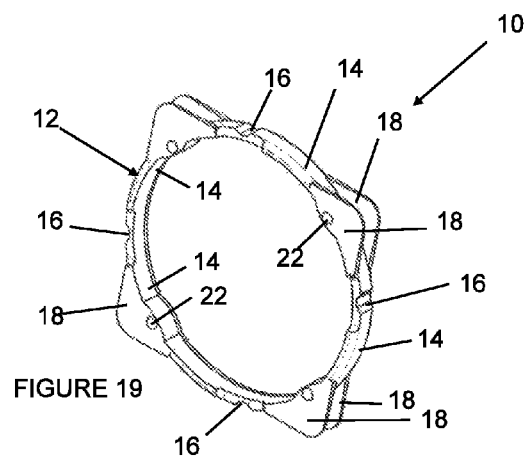

IRIS EXPANDER

CROSS-REFERENCES TO RELATED APPLICATIONS

This application is a continuation of U.S. application Ser. No. 14/216,013, filed on Mar. 17, 2014, now U.S. Pat. No. 8,900,136, which claims priority to U.S. Provisional Patent Application No. 61/788,350, filed Mar. 15, 2013, the entire contents of which are incorporated by reference herein.

BACKGROUND OF THE INVENTION

In order to minimize intra- and post-operative complications from cataract extraction, a surgeon must have the best possible view of intraocular tissue. There may be occasion when a small pupil is encountered, such as with pseudoexfoliation, posterior synechiae, use of miotics, or, uveitis.

If a pupil cannot be properly dilated for cataract extraction, there is risk of: iris damage; incomplete aspiration of lens fragments and cortical material; damage to the posterior capsule; compromised capsulorhexis; loss of vitreous; and, dropped nucleus into the vitreous cavity.

A rise in the incidence of intraoperative floppy iris syndrome, or IFIS, has been noted. Cited results from a retrospective and prospective study indicate that IFIS is encountered approximately 2% of the time. (Chang, D. F., Campbell J. R., "Intraoperative Floppy Iris Syndrome Associated With Tamsulosin", J. Cataract Refract. Surg. 2005; 31: 664-673). Most of the affected patients were found to be taking alpha 1 blockers, such as tamsulosin ("Flomax"), to address benign prostatic hyperplasia. Alpha 1 blockers may cause the iris dilator muscle to relax which makes pupil dilation difficult.

Treatments prior to cataract extraction may include: a pharmacological approach (NSAID's, preservative-free epinephrine, viscoelastic substances); mechanical manipulation (iris hooks/retractors, iris rings/dilators); and, iris surgery.

SUMMARY OF THE INVENTION

In a first aspect of the subject invention, an iris expander is provided which includes a non-metallic, unitary, multi-segmented body which is expandable from a first state to a second state. The second state defines a larger footprint than the first state with the body being defined by a plurality of segments connected by living hinges. Advantageously, with the subject invention, an iris expander may be introduced in a low profile into a patient's eye and expanded therewithin.

In a further aspect of the subject invention, an iris expander is provided which includes a multi-segmented body that is expandable from a first state to a second state. The second state defines a larger footprint than the first state. At least one aperture is formed in the body with a channel extending therefrom into a portion of the body with the channel being embedded in the body such that no portion thereof is exposed externally of the body. The channel is formed to accommodate a portion of an instrument for causing adjustment of the body. Advantageously, with the subject invention, an iris expander may be provided which may be adjusted by an instrument with avoidance of direct contact of the instrument with the tissue of the iris.

These and other features of the invention will be better understood through a study of the following detailed description and accompanying drawings.

BRIEF DESCRIPTION OF THE DRAWINGS

FIGS. 4-6 are different views of a further iris expander formed in accordance with the subject invention;

FIGS. 4A and 4B show different channel configurations useable with the subject invention;

FIGS. 7-10 are different views of the iris expander of FIGS. 4-6 in a collapsed state;

FIGS. 14-16 are different views of an iris expander similar to the iris expander of FIGS. 11-13, but with frame-shaped lobes, in a collapsed state;

FIGS. 17-19 are different views of a further iris expander formed in accordance with the subject invention;

FIG. 20 shows the iris expander of FIGS. 17-19 in a collapsed state; and,

DETAILED DESCRIPTION OF THE INVENTION

Figure 1:
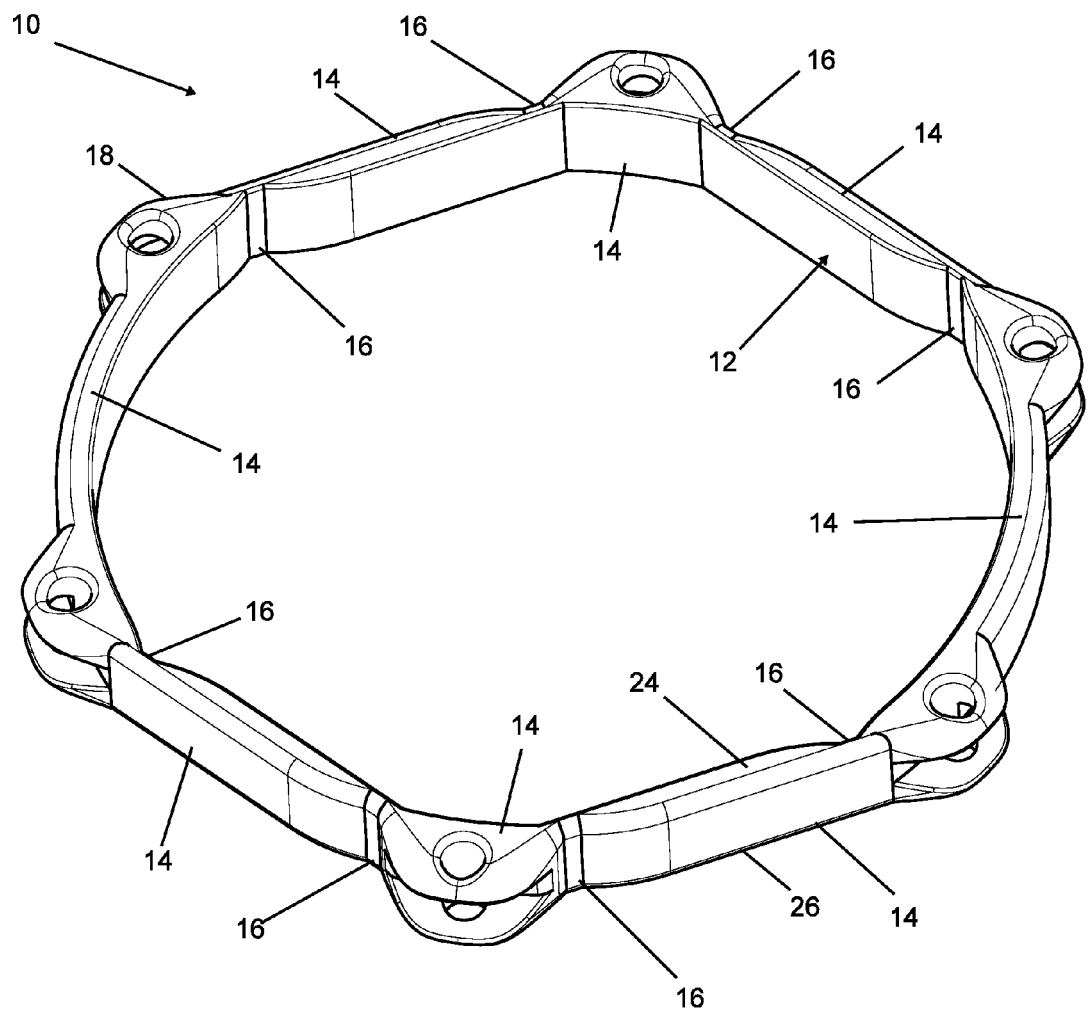
FIG. 1 shows an iris expander formed in accordance with the subject invention.

With reference to the Figures, an iris expander 10 is provided which includes a body 12 which is expandable from a first, collapsed state to a second, expanded state. The body 12 defines a larger footprint in the second state than in the first state. The expansion of the body 12 allows for introduction of the iris expander 10 in a low profile state and expansion in situ to expand an iris for an ophthalmic procedure, such as cataract extraction, and maintenance of that expanded state for the duration of the procedure. After the procedure, the iris expander 10 may be collapsed and removed.

In a first embodiment, the body 12 is multi-segmented and defined by a plurality of segments 14 connected by living hinges 16. With this arrangement, the body 12 may be unitarily formed from non-metallic materials, such as polymeric materials, including, but not limited to, thermoplastics, elastomers and combinations thereof (e.g., copolymers of thermoplastics/elastomers). The body 12 needs to be biocompatible and sterilizable. With the living hinges 16, the segments 14 are pivotable relative to each other to permit the body 12 to be initially prepared in the first state and then expanded to the second state. The living hinges 16 provide pivot points and/or points of relief to facilitate resilient deformation of the segments 14 when in the first state.

The living hinges 16 may be formed by thinned sections of the body 12 so as to define isthmuses between adjacent pairs of the segments 14. The living hinges 16 may be formed with initial forming (e.g., molding) of the body 12 so as to have thin flexible profiles and/or may be prepared by secondary manufacturing processes which allow for material removal (e.g., cutting) to define the thinned sections. The living hinges 16 are sufficiently flexible to permit reversible bending thereof in allowing for angular rotation between two adjacent segments 14 about the joining living hinge 16.

Based on material selection and/or manufacturing technique for the body 12, the body 12 may be adapted to be manually expandable (e.g., where the body 12 is formed of thermoplastic material (e.g., polypropylene)) or to be self-expanding (e.g., where the body 12 is formed of elastomeric or thermoplastic/elastomeric material (e.g., elastomeric polyurethane)). Where the body 12 is adapted to be manually expandable, the living hinges 16 need not be provided with any inherent memory or other bias for expansion of the body 12. Rather, as described below, manual force may be applied to the body 12 to achieve expansion. The living hinges 16 may be formed sufficiently rigid so as to remain in a state once urged into such position (e.g., remain in particular states with the body 12 in the second expanded state). This allows for the body 12 to remain in a fixed state, such as the second state. Alternatively, where the body 12 is adapted to be self-expanding, the living hinges 16 may include inherent memory so as to have an internal bias towards the expanded, second state. Such memory may generate a force urging the living hinges 16 towards the expanded state. This force will also act on the segments 14. Sufficient force must be generated to not only cause expansion of the body 12 but also overcome any resistive force of the iris in causing expansion thereof. Also, the inherent memory will impart a force to the living hinges 16 to maintain the living hinges 16 in the expanded state. Preferably, the body 12 is initially formed in the second, expanded state where self-expanding is desired.

The body 12 is formed as a closed loop which is intended to engage the margin of the iris with at least portions of, preferably the entirety of, its outer perimeter when in the expanded state. The body 12 can be of various shapes, including being elliptical (e.g., circular) or polygonal (e.g., square). It is preferred that the segments 14 and the living hinges 16 extend continuously about the length of the body 12 without any interruptions so as to prevent any portion of the iris to extend through the body 12. It is further preferred that the body 12 be generally planar with expansion from the first state to the second state occurring in a single expansion plane.

It is envisioned that irises of 5.0 mm or less may require expansion to allow for proper visual access into the eye during an ophthalmic procedure. It is preferred that the footprint of the body 12 in the second state, as defined by outer side surface 29 of the body 12 (FIGS. 4, 4A, 4B), define a diameter of at least 6 mm, more preferably at least 7 mm.

Figure 2:
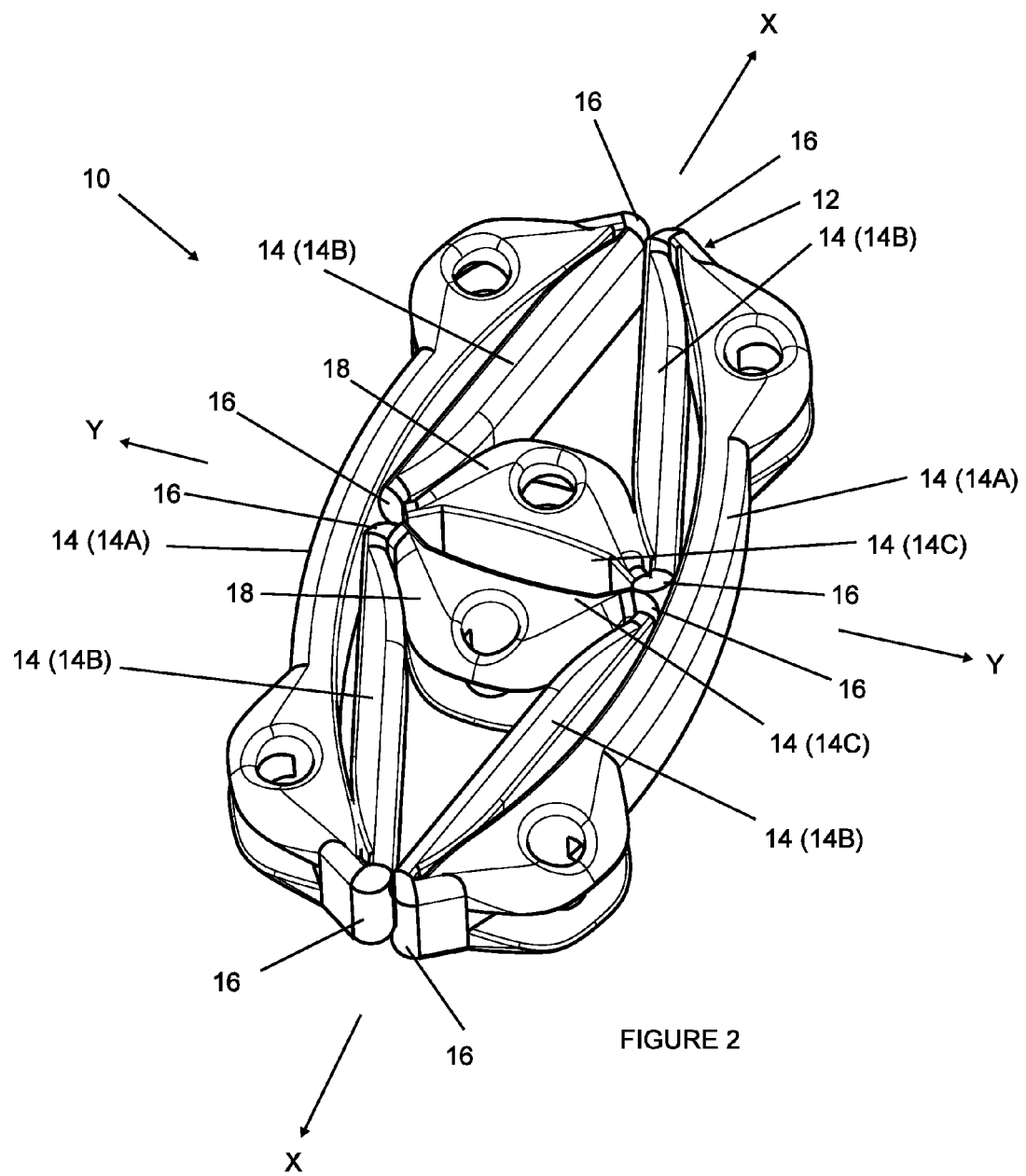
FIG. 2 shows the iris expander of FIG. 1 in a collapsed state.

With reference to the Figures, the segments 14 can be provided in various lengths and shapes to provide desired first and second states of the body 12. The body 12 in the second state may have a generally circular shape. In one variation, as shown in FIGS. 1 and 2, eight of the living hinges 16 may be provided which separates the body 12 into eight of the segments 14, the segments 14 not being of equal length. As shown in FIG. 2, primary segments 14A are each provided with an arcuate shape with the primary segments 14A being positioned to bow outwardly from each other with the body 12 being in the first state. The remaining segments 14 are configured to be located within the primary segments 14A with the body 12 being in the first state. By way of non-limiting example, four secondary segments 14B may be provided each of generally the same length with one of the secondary segments 14B extending from each end of the primary segments 14A. Two tertiary segments 14C are provided which each connect a pair of the secondary segments 14B. With this arrangement, as shown in FIG. 2, the secondary segments 14B and the tertiary segments 14C may be folded and maintained inside of the primary segments 14A as shown. Lobes 18 formed on the body 12 should be configured to minimally inhibit, if not avoid altogether inhibiting, full collapsing of the body 12, particularly where the lobes 18 are located interiorly of at least some of the segments 14 with the body 12 in first state. Thus, the lobes 18 formed on the tertiary segments 14C should be shaped to not inhibit full collapsing of the secondary segments 14B inside of the primary segments 14A.

With reference to FIGS. 4-19, the body 12 may be formed with the segments 14 being of equal lengths. FIGS. 4-10 show the body 12 having eight of the living hinges 16 which separates the body 12 into eight of the segments 14. Alternatively, as shown in FIGS. 11-19, the body 12 may be formed with four of the living hinges 16 separating the body 12 into four of the segments 14.

The locations of the living hinges 16 and the lengths of the segments 14 will affect the configuration of the body 12 in the first state. FIG. 2, discussed above, provides a first state which is expandable outwardly along two Cartesian axes (represented in FIG. 2 by "X" and "Y" arrows). FIGS. 7-10, 11-13 and 14-16 each show the body 12 in a first state which is expandable outwardly along one Cartesian axis (represented in FIG. 7 by "X" arrows). Here, the body 12 is collapsed about two of the living hinges 16, which may be opposing, to define first and second ends 32, 34. The lobes 18 are located exteriorly of all of the segments 14. The body 12 may foreshorten along the perpendicular Cartesian axis during expansion (represented in FIG. 7 by "Y" arrows) with this configuration. Living hinges 16 may be located at various mid-points between the first and second ends 32, 34 depending on the lengths of the corresponding segments 14. Where the segments 14 are of equal length, the living hinges 16 will be located generally centrally between the first and second ends 32, 34. The living hinges 16 not located at the ends 32, 34 may act as points of relief to facilitate resilient deformation of the segments 14 in the first state. This allows for the segments 14 to have natural at-rest arcuate shapes in the second state, yet be deformed to generally straight shapes with the body 12 in the first state. The release of the segments 14 from the deformed straight states to their natural at-rest states may impart force of expansion to the body 12 where self-expansion thereof is desired.

One or more of the lobes 18 may be provided on the body 12 for extending over a portion of the iris during implantation and/or expansion of the iris expander 10. A plurality of the lobes 18 may be spaced about the body 12 at equal intervals along a single edge of the body 12, such as first edge 24 of the body 12. The lobes 18 are positioned so that a portion of the iris is received adjacent thereto. This provides a locating function for the iris expander 10 relative to the iris and additional stability in while expanding the body 12 and holding the body 12 in the expanded state.

Figure 3:
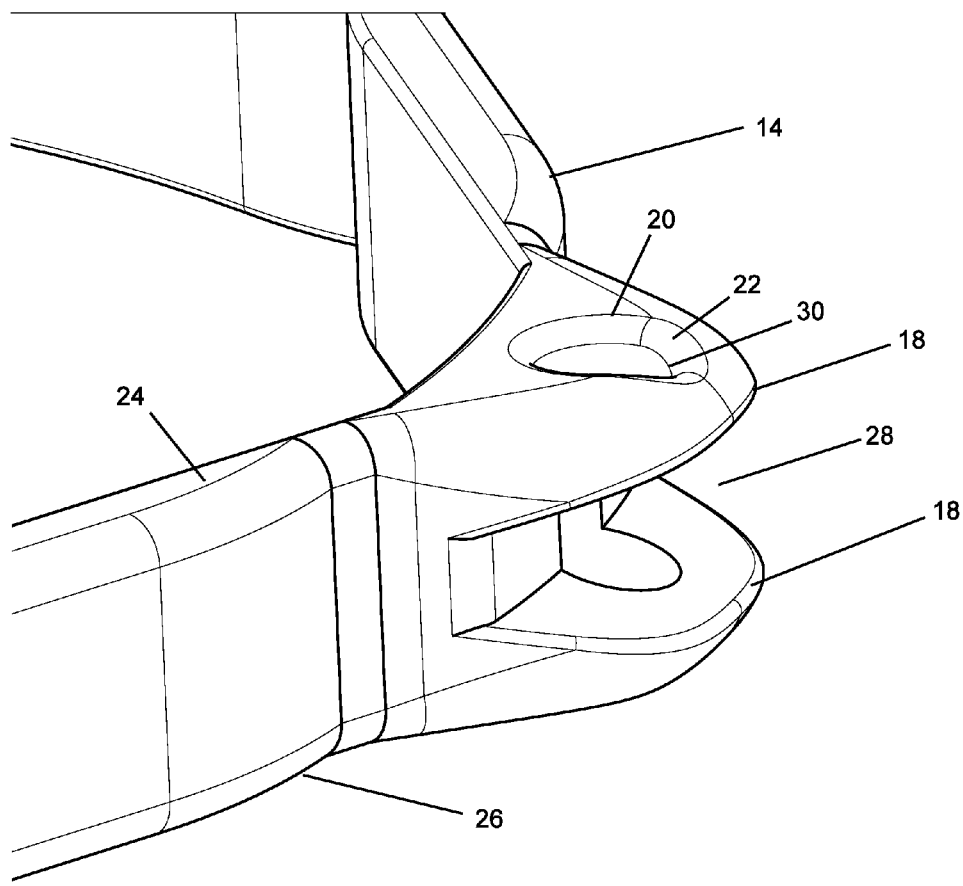
FIG. 3 shows lobes useable with the subject invention.
Figure 11:
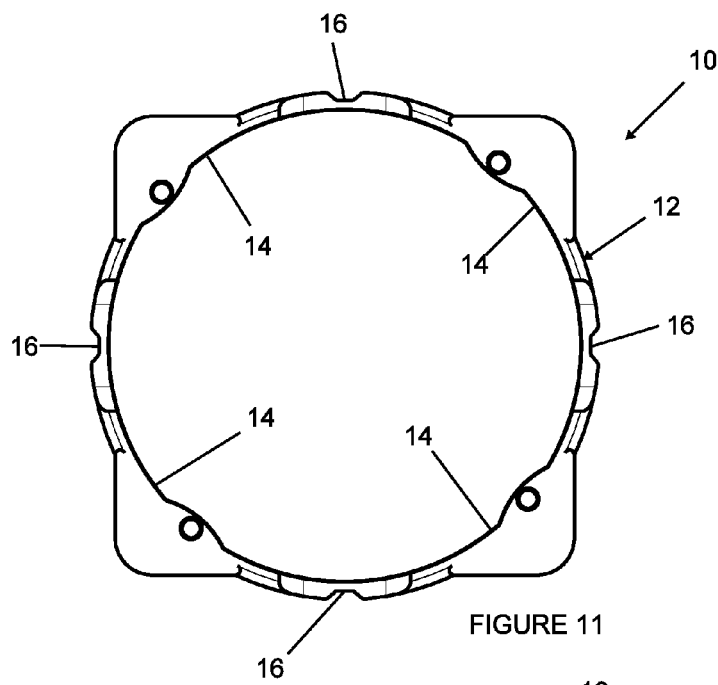
FIGS. 11-13 are different views of a further iris expander formed in accordance with the subject invention.
Figure 12:
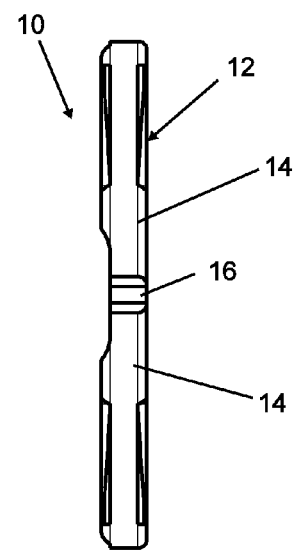
Figure 13:
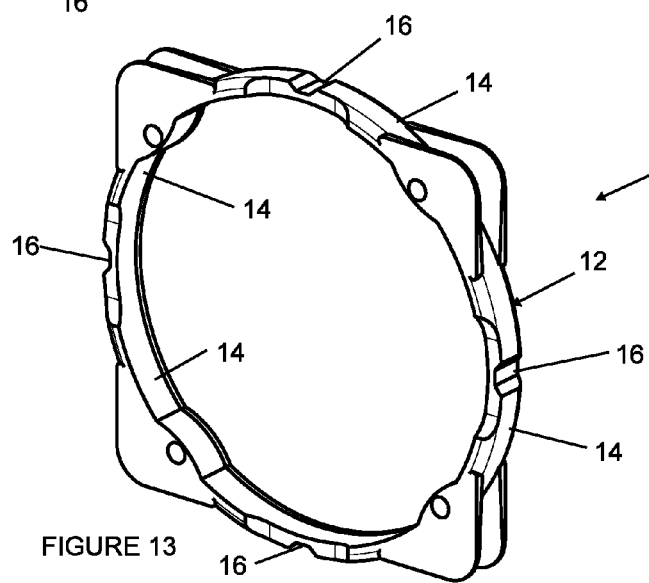

With reference to FIG. 3, the lobes 18 may be provided along both the first edge 24 and second edge 26 of the body 12. The lobes 18 on the first and second edges 24, 26 may be aligned about the perimeter of the body 12 so as to form U-shaped pockets 28 directly between a pair of the lobes 18 located above and below. The pockets 28 may receive portions of the iris. Alternatively, with reference to FIGS. 4-6, the lobes 18 may be spaced in equal intervals about each of the first edge 24 and the second edge 26 but out of phase between the first and second edges 24, 26 so that the lobes 18 alternately protrude from the opposing edges 24, 26 about the body 12. This arrangement provides upper and lower stabilization without defining the pockets 28.

The lobes 18 may be formed solidly (FIG. 3) so as to be continuous or frame shaped (FIG. 14) with portions thereof being open. In addition, the lobes 18 may be located centrally (FIG. 4) or off-center (FIG. 17) on the segments 14. This allows for different positions of the lobes 18 with the body 12 in the first state, as shown in comparing FIGS. 14-16 and FIG. 20.

As shown in FIG. 3, one or more of the lobes 18 may include an aperture 20 from which extends a channel 22. The channel 22 is formed to accommodate a portion of an instrument for positioning the body 12 and/or causing expansion of the body 12. The channel 22 may be blind or may extend through the respective lobe 18 to a second aperture 30 so as to be exposed externally of the adjacent segment 14. If the lobes 18 are frame shaped, the instrument may be inserted into an open portion thereof.

In a second embodiment of the invention, and with reference to FIGS. 4-19, the channel 22 is located to extend through one of the segments 14 with the aperture 20 being exposed on the first edge 24 of the body 12 along the corresponding segment 14. In this manner, the channel 22 is embedded in the segment 14 with no portion thereof exposed externally of the body 12, as shown schematically in FIGS. 4A and 4B. The channel 22 is completely spaced inwardly from both inner side surface 27 and the outer side surface 29 of the body 12. This arrangement locates an instrument received in the channel 22 out of axial alignment with the iris tissue. The channel 22 may be blind (FIG. 4A) or may extend to the second aperture 30 (FIG. 4B) which is exposed externally on the second edge 26. With this arrangement, an instrument engaged in the channel 22 is located inwardly of the margin of the iris. Thus, even with the instrument extending through the second aperture 30, the instrument does not directly contact the iris. Preferably, the channel 22 extends along a longitudinal axis which is transverse to the expansion plane. Further, a plurality of the channels 22 may be provided in the body 12, each with a corresponding aperture 20. The channel 22 may be evenly spaced about the body 12. In addition, one of the lobes 18 may be located adjacent to each of the channels 22. This allows for additional tissue stabilization at potential locations of force application for expansion.

With respect to the second embodiment, the placement of the channel 22 wholly within the body 12 may be utilized with various configurations of the body 12 as described above with respect to the first embodiment. The body 12 can be multi-segmented with a plurality of the segments 14. However, the living hinges 16 are not required for the second embodiment of the invention; various hinges, and other connections, between the segments 14 may be utilized. In all other respects, the second embodiment may be practiced in the same manner as the first embodiment.

Figure 21:
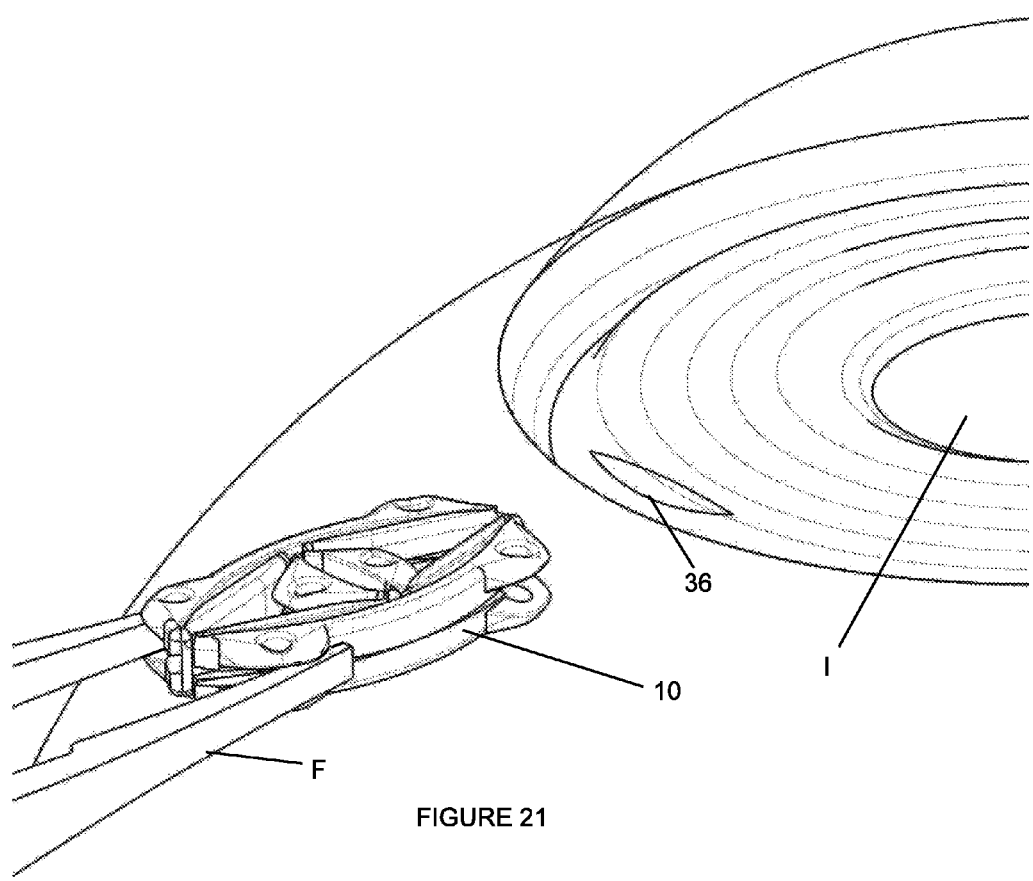
FIGS. 21-29 show various aspects of introducing and using an iris expander formed in accordance with the subject invention.
Figure 22:
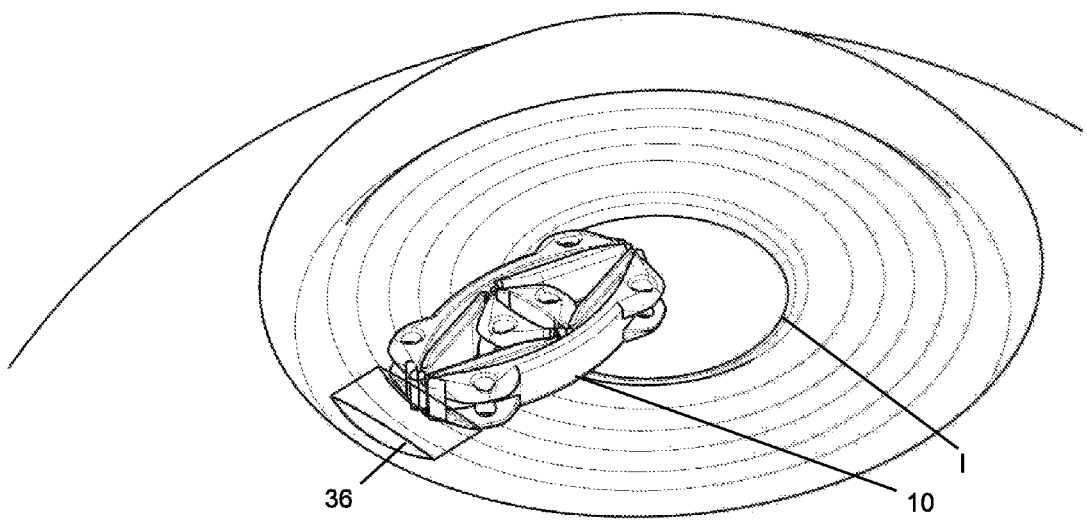
Figure 23:
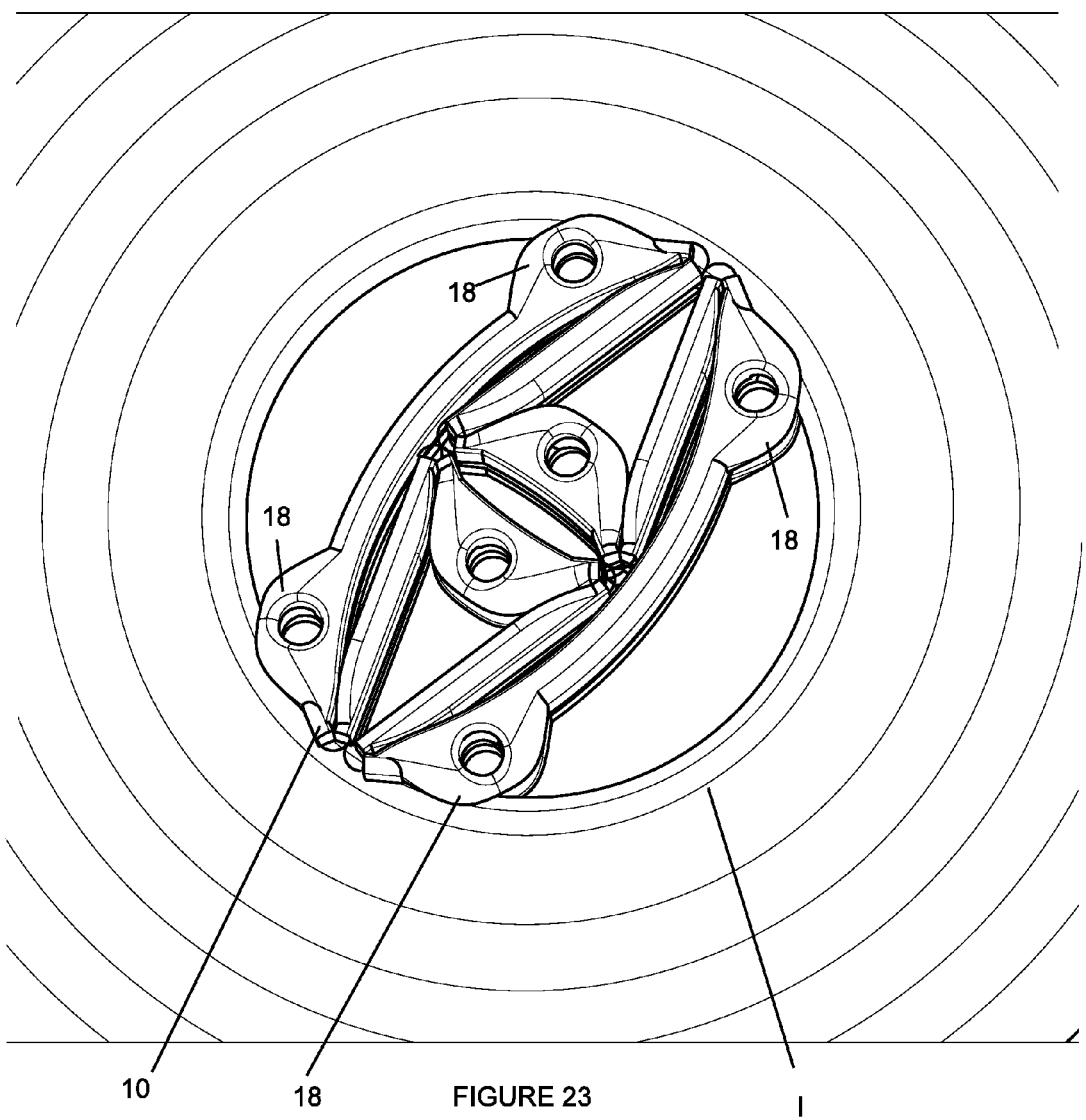
Figure 24:
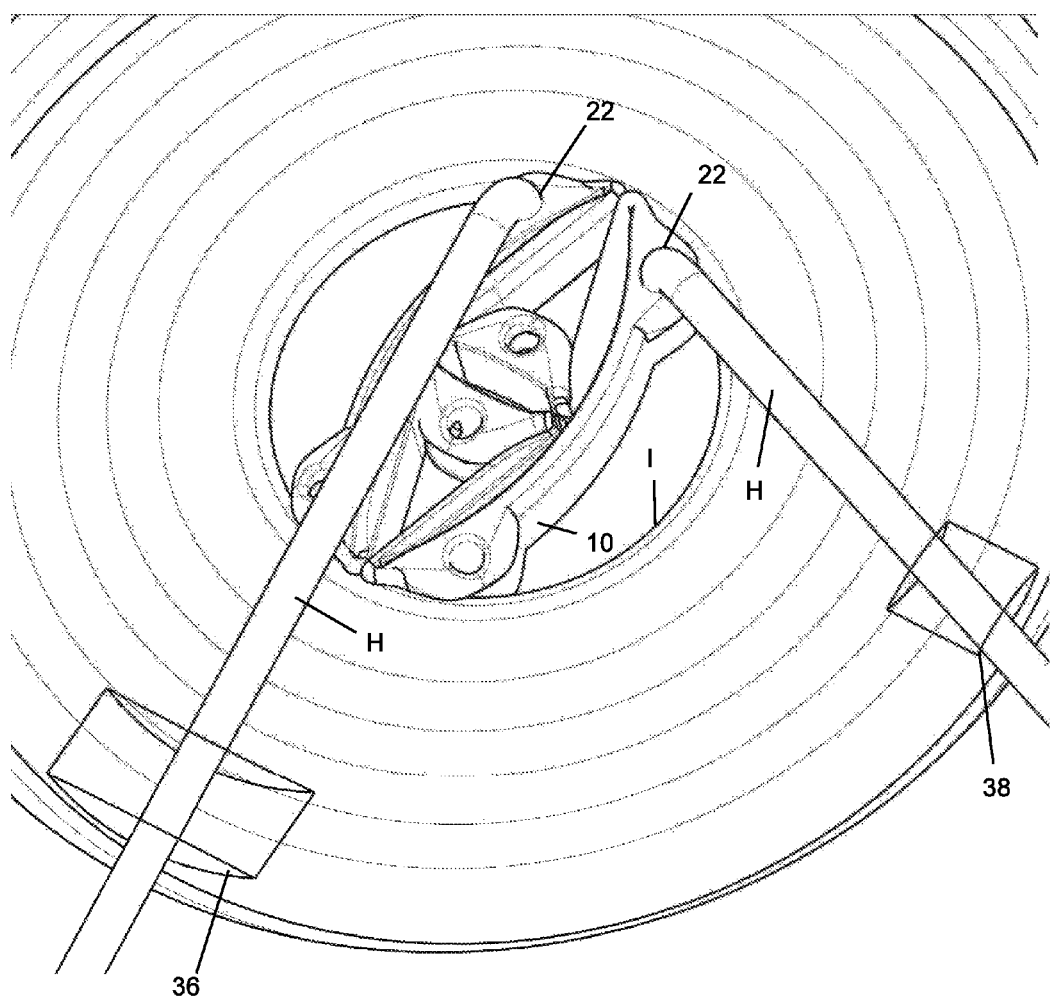
Figure 25:
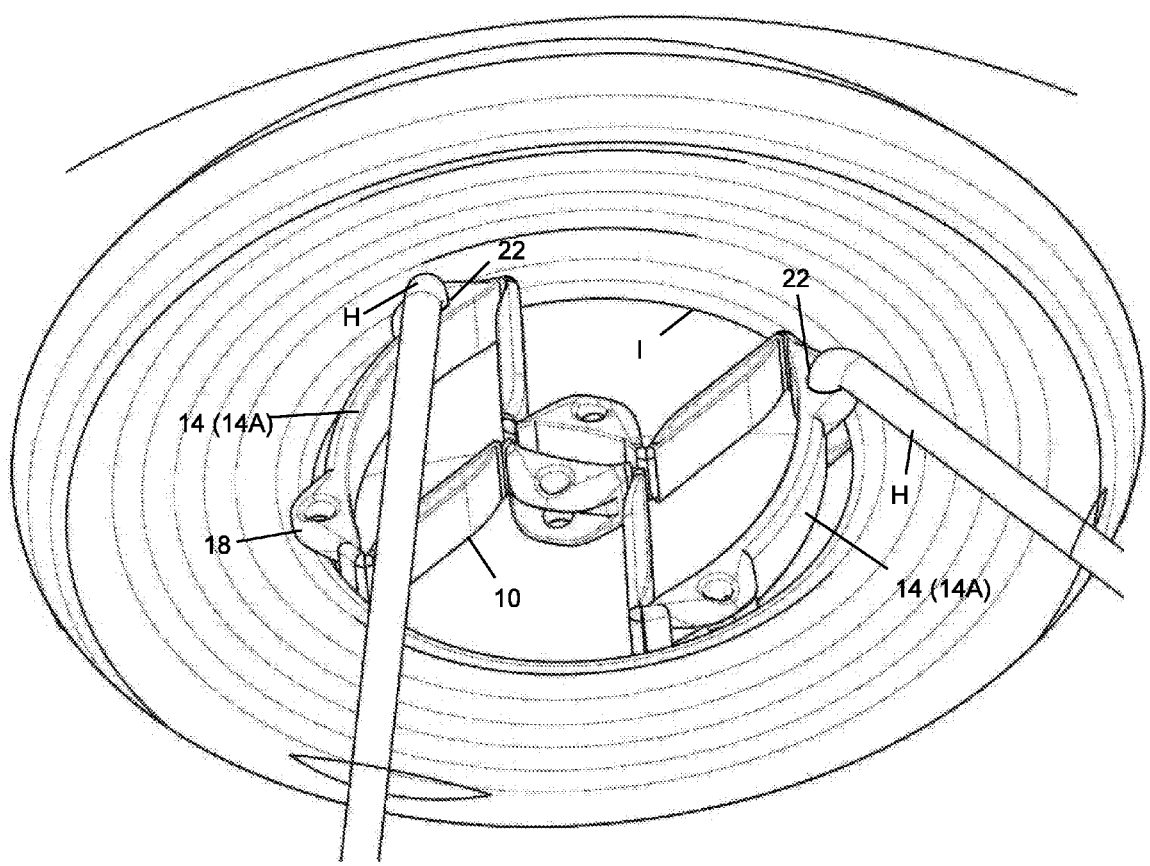
Figure 26:
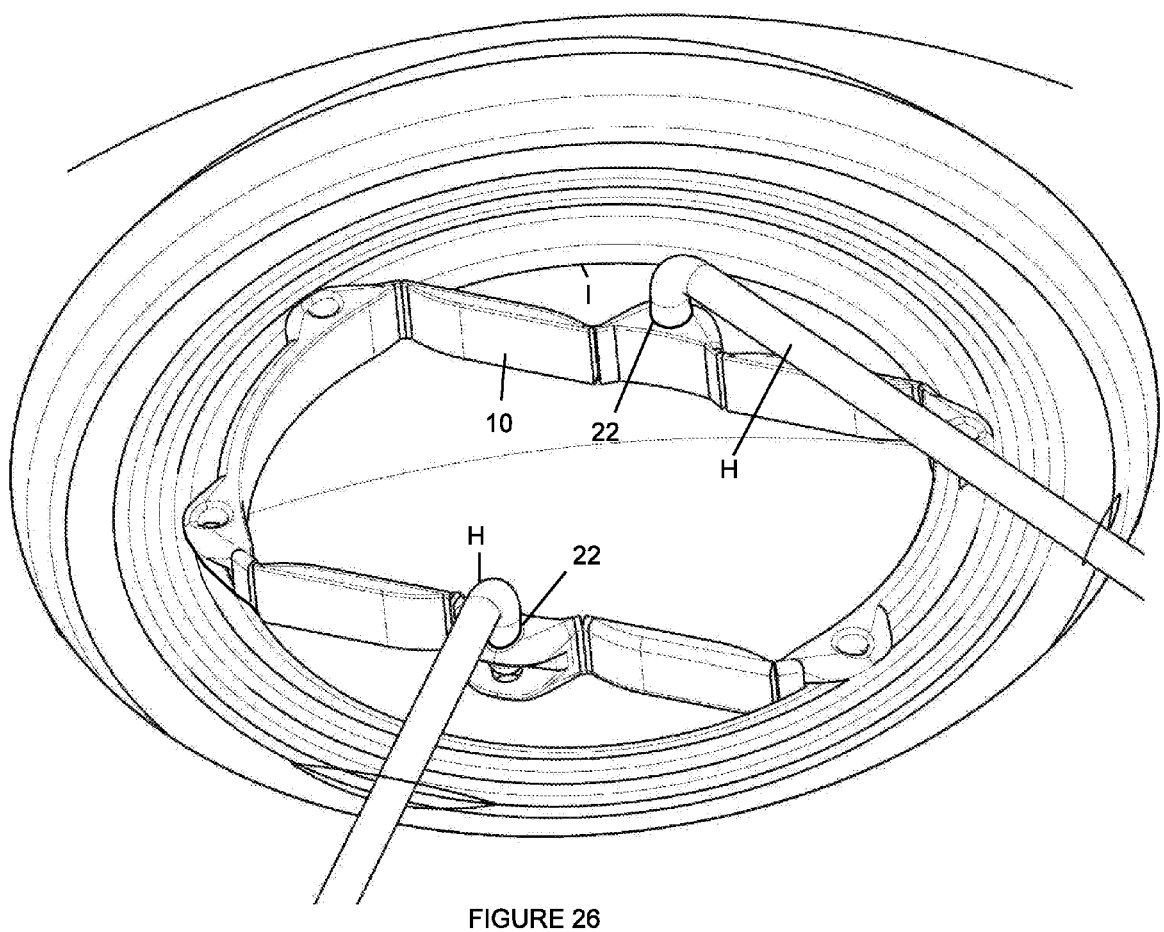
Figure 27:
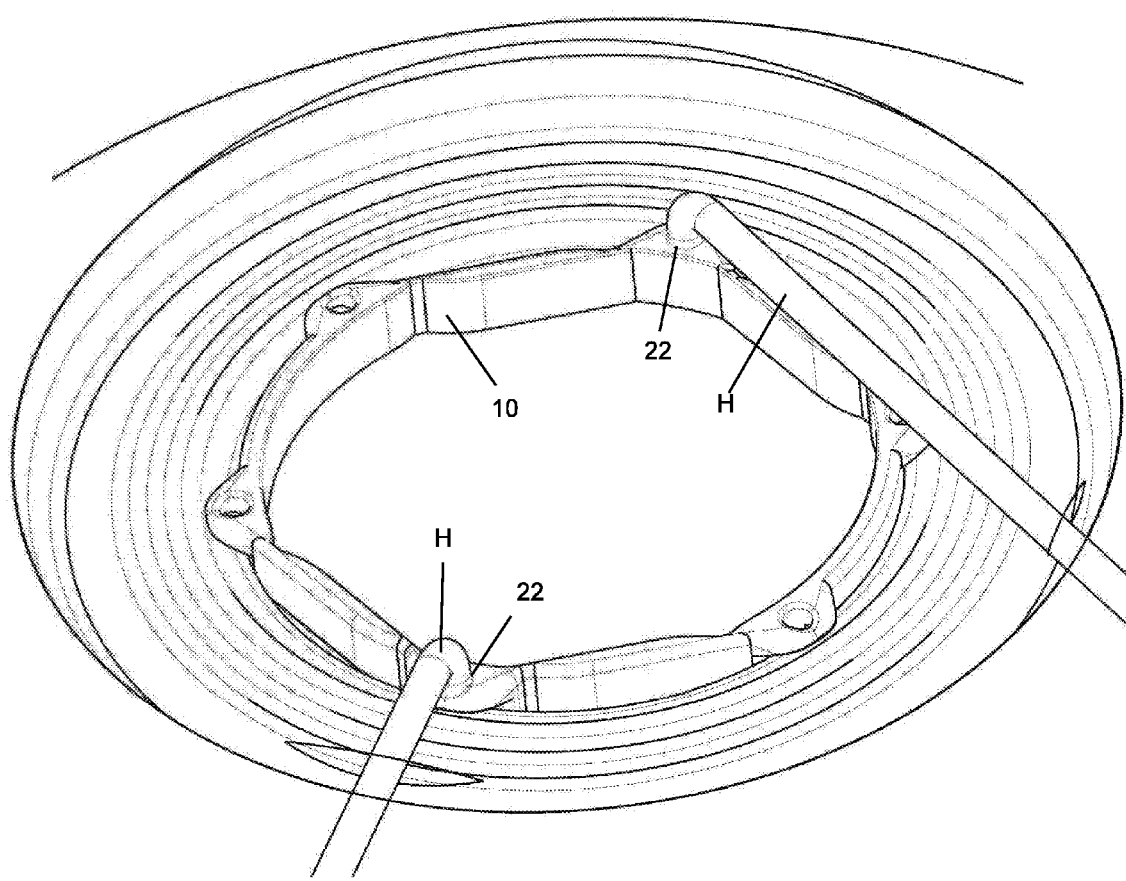
Figure 28:
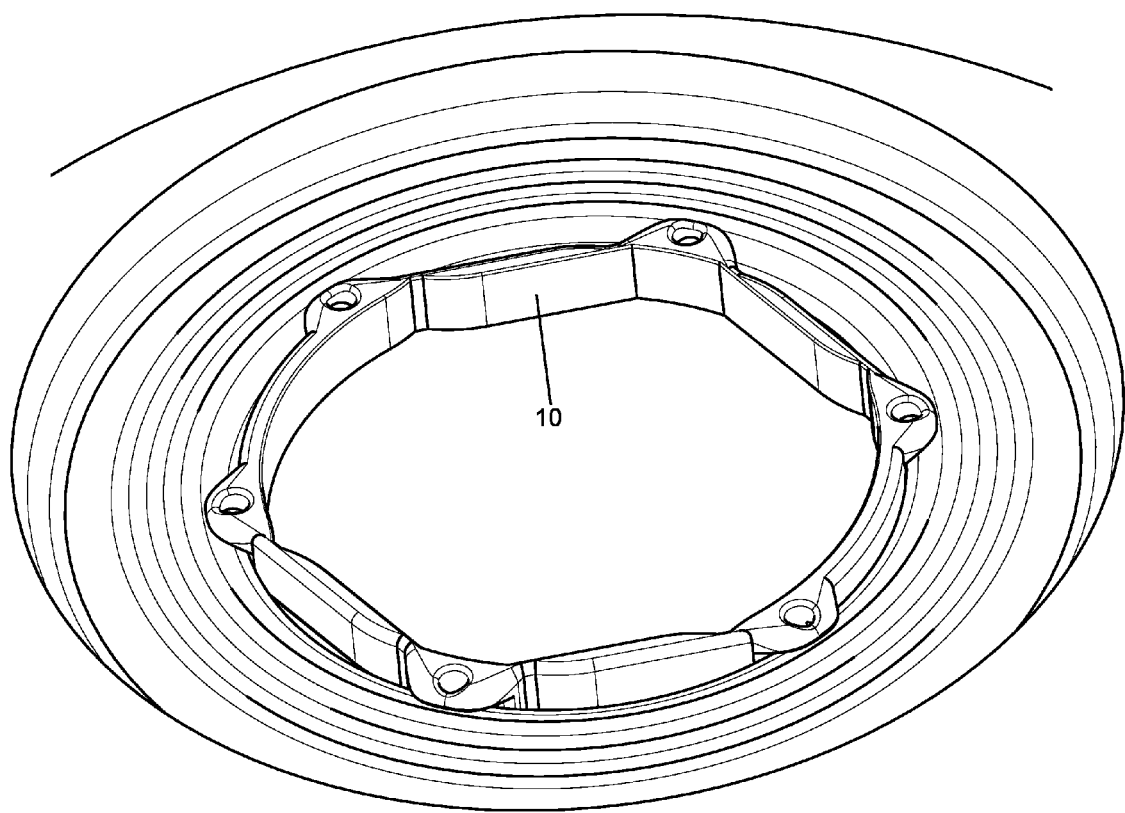

With reference to FIGS. 21-29, various aspects of introducing and using the iris expander 10 is shown. Although a specific shape of the body 12 is shown, it is to be understood that the body 12 can be formed with any configuration discussed herein, including both the first and second embodiments. With reference to FIG. 21, a corneal incision 36 is initially made in a patient's eye to be treated. A typical corneal incision for cataract extraction may be utilized. The iris expander 10 is introduced into the eye with the body 12 being in the first, collapsed state. With the iris expander 10 being manually expandable, forceps F or other instruments may be used to insert the iris expander 10 through the corneal incision 36 and locate the iris expander 10 within the iris I. Thereafter, the iris expander 10 is positioned so that the iris margin is aligned with at least a portion of the lobes 18 (FIG. 23). One or more instruments, such as hooks H (e.g., Sinskey hooks), may be used to properly position the iris expander 10 (FIG. 24). Secondary incisions 38 in the cornea may be utilized as needed. Preferably, as shown in FIG. 25, the iris expander 10 is manually expanded by applying force in generally opposing directions. As shown here, certain segments 14, such as the primary segments 14A, may be first extended outwardly. This partial expansion of the iris expander 10 allows for partial expansion of the iris I. Thereafter, remaining portions of the body 12 may be expanded, such as shown in FIG. 26. This continues until full expansion of the iris expander 10 is achieved. Once fully expanded (FIG. 28), an ophthalmic procedure may be conducted. After the procedure, the iris expander 10 is collapsed and removed using a reverse procedure.

Figure 29:
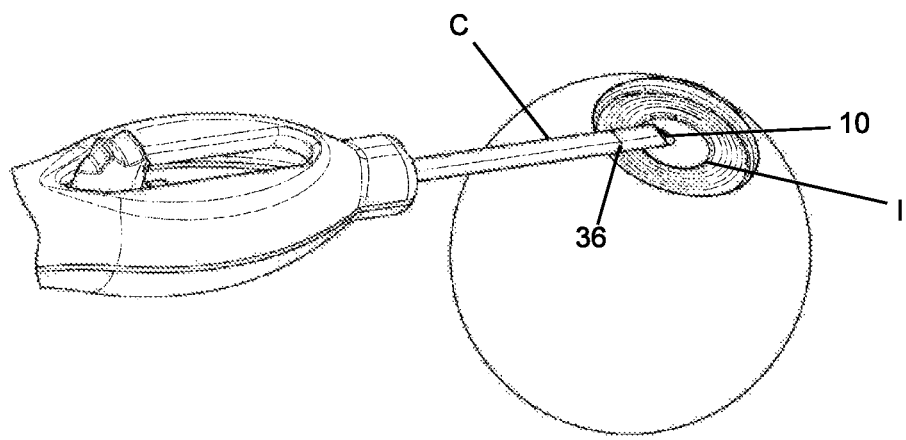

With self-expansion, the iris expander 10 may be maintained in the first state by an introducer C inserted through the corneal incision 36 (FIG. 29). The introducer C (e.g., a pusher plunger instrument) urges the iris expander 10 therefrom to be located within the iris I. With release, the iris expander 10 expands to the second state. An instrument, such as one or more hooks (e.g., Sinskey hooks), may be used to adjust the position of the iris expander 10 as necessary. Once fully expanded (FIG. 28), an ophthalmic procedure may be conducted. After the procedure, the iris expander 10 is collapsed, e.g., by retraction into the introducer C.

What is claimed is:

1. An iris expander for acting against a margin of an iris of a patient's eye in causing expansion of the iris, the iris expander comprising:
a closed-loop, multi-segmented body which is expandable from a first state to a second state, said second state defining a larger footprint than said first state, said body being defined by a plurality of segments connected by hinges, at least one aperture, spaced from said hinges, being formed in a first of said segments with a channel extending therefrom into a portion of said first segment, said channel being embedded in said first segment such that no portion thereof is exposed externally of said first segment, wherein, with the iris expander acting against the margin of the iris of the patient's eye, said channel being formed to accommodate a portion of an instrument inwardly of the margin of the iris without the accommodated portion of the instrument contacting the iris.

2. An iris expander as in claim 1, wherein said channel terminates at a second aperture formed in said first segment.

3. An iris expander as in claim 1, wherein expansion of said body in expanding from said first state to said second state is generally in an expansion plane.

4. An iris expander as in claim 3, wherein said channel extends along a longitudinal axis disposed transverse to said expansion plane.

5. An iris expander as in claim 1, wherein said hinges are living hinges.

6. An iris expander as in claim 1, wherein a plurality of said apertures, each spaced from said hinges, are provided about said segments, a channel extending from each said aperture which is embedded in respective said segment such that no portion thereof is exposed externally respective said segment.

7. An iris expander as in claim 6, wherein said plurality of apertures are evenly spaced about said body.

8. An iris expander as in claim 1, wherein said body is non-metallic.

9. An iris expander as in claim 8, wherein said body includes elastomeric material.

10. An iris expander as in claim 8, wherein said body includes thermoplastic material.

11. An iris expander as in claim 8, wherein said body includes thermoplastic/elastomeric copolymer.

* * * * *